United States Patent [19]

Hamann et al.

[11] Patent Number: 5,748,311

[45] Date of Patent: May 5, 1998

[54] APPARATUS AND METHOD OF PARTICLE GEOMETRY MEASUREMENT BY SPECKLE PATTERN ANALYSIS

[76] Inventors: Oliver Hamann, Holzhaeuser Weg 41c, 21217 Seevetal; Reinhard Ulrich, Alte Rennbahn 2, 21244 Buchholz, both of Germany

[21] Appl. No.: 614,937

[22] Filed: Mar. 11, 1996

[51] Int. Cl.[6] ............................ G01N 15/02; G01N 21/00
[52] U.S. Cl. ..................... 356/336; 356/338; 356/342; 356/364; 356/73; 250/574
[58] Field of Search ............................ 356/335–336, 356/338, 342, 364, 73; 250/574

[56] References Cited

U.S. PATENT DOCUMENTS

| | | | |
|---|---|---|---|
| 3,721,500 | 3/1973 | Fugitt | 356/342 |
| 4,457,624 | 7/1984 | Goldbent et al. | 356/342 |
| 4,572,664 | 2/1986 | Hauson | 356/342 |
| 5,063,301 | 11/1991 | Turkevich et al. | 356/342 |

OTHER PUBLICATIONS

Bauckhage, Klaus, "The Phase–Doppler–Difference–Method, a New Laser–Doppler Technique for Simultaneous Size and Velocity Measurements, Part I: Description of the Method", *Part. Syst. Charact.* 5, pp. 16–22 (1988).

Bauckhage, Klaus et al., "The Phase–Doppler–Difference–Method, a New–Laser–Doppler Technique for Simultaneous Size and Velocity Measurements, Part 2: Optical Particle Characteristics as a Base for the New Diagnostic Technique", *Part. Part. Syst. Charact.* 5, pp. 66–71 (1988).

Dainty, John C., "Laser Speckle and Related Phenomena", *Springer–Verglag Berlin Heidelberg New York*, pp. 1–75 (1975).

Etzler, Frank M. et al., "Particle Size Analysis: a Comparative Study of Various Methods", *Part. Part. Syst. Charact.* 12, pp. 217–224 (1995).

van de Hulst, H.C., "Light Scattering by small particles", *Dover Publications, Inc.*, pp. 63–131 (1957).

*Primary Examiner*—Frank G. Font
*Assistant Examiner*—Jason D. Vierra-Eisenberg
*Attorney, Agent, or Firm*—Christensen O'Connor Johnson & Kindness

[57] ABSTRACT

The invention provides a method and a system for measuring geometric properties, such as diameter, shape and surface roughness of single rough particles by an optical method. The particle may be immersed in a gaseous or liquid fluid. A volume of the fluid, containing the particles to be measured, is illuminated by a beam of coherent electromagnetic radiation, resulting in a distribution of scattered radiation with a speckle structure. This distribution is detected with a one-dimensional or two-dimensional image detector. An autocorrelation function RI(r) of the detected intensity distribution is calculated, and from the position δr of its first zero the diameter $d_P$ of the scattering particle is evaluated based on I, the wavelength of the electromagnetic radiation, and $Z_0$, the distance from the particle to the detector. The system to perform this method comprises a radiation source, which is preferably a laser, to illuminate a measuring volume, and an array or matrix detector arranged to receive the backscattered light. The detected intensity distribution is converted to binary data and a signal processing unit calculates the autocorrelation function of the detected intensity distribution to yield the particle size. In a preferred embodiment of the invention, the radiation scattered from a particle is relayed to the detector by an optical system comprising a set of lenses, a polarizer and a pinhole. The surface roughness of the particle under investigation is estimated from the contrast of the measured intensity distribution. The shape of the particle follows from an evaluation of the calculated diameter values along a set of angular directions $\phi = 0 \ldots \pi$.

24 Claims, 4 Drawing Sheets

APPARATUS AND METHOD OF PARTICLE GEOMETRY MEASUREMENT BY SPECKLE PATTERN ANALYSIS

FIELD OF THE INVENTION

The invention relates to the field of particle size measurement. In particular, the invention provides a method and system for measuring dimensions and surface characteristics of an individual particle by observing and analyzing the intensity distribution of coherent electromagnetic radiation backscattered from the particle.

BACKGROUND OF THE INVENTION

The size of particles immersed and flowing in a gaseous or liquid fluid is often an important parameter of certain industrial processes, including chemical processes, combustion processes, and the like. Particles found in these processes vary widely in size, shape, structure and material. Numerous methods have been developed for the in situ characterization of particle parameters, and a survey of current methods is given in T. Allen, "Particle Size Measurement", Chapman and Hall, London (1990).

It is generally believed that optical methods of particle measurement are advantageous in applications where particle densities are relatively moderate. Instruments using optical methods allow non-contact measurement of the particles so that the flow of the particles is substantially unaffected by these methods. Most optical methods operate on the same broad principle: the particles under investigation are illuminated, part of the illuminating light is scattered, and particle characteristics such as size or shape are determined from an analysis of the scattered light. However, there are many variations possible within this principle. For example, the size of the particle relative to the wavelength of the illuminating light is an important consideration. The particles may be very small as compared to the wavelength of the illuminating light, the particles may be comparable in size to the wavelength of the light, or the particles may be much larger than the wavelength of the light. For each of these three regimes models that describe light scattering from idealized particles are shown in the literature, and usually form extensions of the general Mie-theory (see for example H. C. Van de Hulst, "Light Scattering by Small Particles", Dover Publications, New York (1981)).

Optical methods that measure particles which are large compared to the illuminating wavelength include methods which use the scattered light from groups of particles, and also methods which measure the scattered light from single particles. The techniques that utilize scattered light from groups of particles include the Fraunhofer-diffraction instruments, also known as laser-diffraction-spectrometers. These instruments measure scattered intensity distributions near forward angles. The Fraunhofer-diffraction instruments are widely used and are generally well suited for spherical, homogenous particles, such as aerosols. However, they fail to give accurate size distributions for irregularly shaped particles. This shortcoming is shown in, for example, F. M. Etzler, M. S. Sanderson, "Particle Size Analysis: a Comparative Study of Various Methods", Part. Part. Syst. Char., 12 (1995).

Another category of instruments using measurements of groups of particles evaluates the extinction of a wide beam of light passing through the group of particles. These instruments provide a mean particle size, if the concentration of particles in the group is known. In general, they cannot provide a size distribution of the particles.

The Phase-Doppler-Anemometry (PDA) technique optically measures the size of single particles. These instruments utilize back-scatter intensity measurements. PDA is well suited for size measurement of spherical homogenous particles, such as aerosols or sprays. However, particles with rough surfaces are usually not measurable by PDA, as explained for example in K. Bauckhage, "The Phase-Doppler-Difference-Method, a New Laser-Doppler-Technique for Simultaneous Size and Velocity Measurements", Part. Part. Syst. Char., 5 (1988).

Surface quality also presents a problem in instruments that measure the absolute intensity of light scattered from a single particle. Small, highly reflective particles give the same backscatter reading as larger, less reflective particles. Therefore, the measurement of absolute backscattered intensity may be misleading. These instruments must be calibrated, using all relevant types of particles that might be encountered, immersed in the fluid under investigation. These instruments generally cannot provide information about particle shape.

Another method of particle size measurement, which may be used with single particles or groups of few particles, is microscopy in combination with image analysis. While microscopy gives the most complete information about particle size and shape, for small particles expensive high-quality optics and high-speed image processing is necessary for on-line measurements. These requirements hinder the application of this technique in in situ investigations of particles immersed in a fluid. Therefore, microscopy is generally used only as a reference measurement in the laboratory.

Nevertheless, there exists a need in the art for an optical system that is able to measure in situ the size of rough, irregularly shaped particles. There is a particular need for such measurements when the particles of a given process have different reflectivities. Such a situation exists, for instance, in the exhaust flue of a coal-combustion plant. Typically, more than 90% of the solids mass flow during this process has particles larger than about 10 microns. Ideally, an optical particle size analyzer could determine the concentration of particles in the fluid (the combustion zone) and the size distribution in situ, and in real time. This information could then be used to control the combustion process so that solids emissions are reduced. The need for such a system also exists in other industrial applications, for example where the size of a rough particle has to be monitored to ensure process quality. These applications include grinding and milling processes, and those processes where a catalyst undergoes degradation that is measurable by a change in particle size or surface roughness, or both.

It is known that a random spatial distribution of light intensity is formed when a beam of substantially coherent light is reflected from a rough surface. This intensity distribution is called a "speckle pattern". The structure or distribution of the speckle pattern depends on the coherence properties of the incident light and the surface characteristics of the rough surface. The statistical properties of speckle patterns have been investigated by a number of authors. See e.g., J. W. Goodman, "Statistical Properties of Laser Speckle Patterns" in *Laser Speckle and Related Phenomena*, Editor J. C. Dainty, Springer, Berlin (1975). A number of optical methods of measurement utilize speckle patterns, and changes in speckle patterns, that arise when coherent light is scattered from a rough surface. None of the known techniques, however, employs the statistical properties of the speckle pattern to determine geometric properties of particles.

SUMMARY OF THE INVENTION

The invention provides a method, and system utilizing the method, for measuring geometric properties of individual particles with rough surfaces. The method uses a coherent illuminating beam of electromagnetic radiation, sized to exceed the largest dimension of the particle, that has a wavelength less than the size of the particle. The intensity distribution, or speckle pattern, of the backscattered light is analyzed to determine particle size and surface characteristics. The invention is applicable to individual particles immersed in gaseous or liquid fluids.

While the invention is also suitable for measuring size parameters of relatively smooth particles, the invention is particularly applicable to rough, irregularly shaped particles. As explained above, prior art methods encounter serious problems in measuring parameters of these rough particles. Moreover, the method of the invention provides an estimate of surface roughness of an individual particle being investigated.

The method of the invention for measuring geometric properties of particles includes illuminating a volume or zone that contains the particle to be measured with an essentially monochromatic beam of electromagnetic radiation. The beam has a wavelength much less than the size of the particle, and a width wider than the largest dimension of the particle. The angular intensity distribution of backscattered electromagnetic radiation is detected and analyzed to determine the geometric properties of the particle, including its size and surface roughness.

The system of the invention for measuring the size and surface roughness of a small particle immersed in a fluid includes a source of electromagnetic radiation of a desired wavelength, less than the size of the particle. In certain embodiments, the system includes a means, such as a prism, for directing the electromagnetic radiation from the source into the volume that contains the particle to be measured. The system also includes a detector for detecting the intensity distribution of backscattered electromagnetic radiation from the surface of the particle. This detector is in electronic communication with a digital signal processor programmed to analyze the intensity distribution and provide the particle size and its surface roughness. Optionally, the digital signal processor is linked to a video display screen to provide an image of the speckle pattern formed by the rough particle.

The invention utilizes a combination of apparatus, such as optical lenses, optical prisms, pin holes, light detectors, digital signal processors, and video display screens, to provide a robust and commercially useful system that can be used to detect the size and surface properties of individual particles in situ, and in real time. This allows control of industrial processes, such as combustion processes, chemical processes, and size reduction processes that are controlled, influenced by or characterized by, the size and shape of particles. Since the system of the invention provides real-time information, the information may be used to optimize process variables to produce products of optimum quality, or generally enhance the efficiency of the process.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, none to scale, wherein.

DETAILED DESCRIPTION OF THE PREFERRED EMBODIMENT

Figure 1:
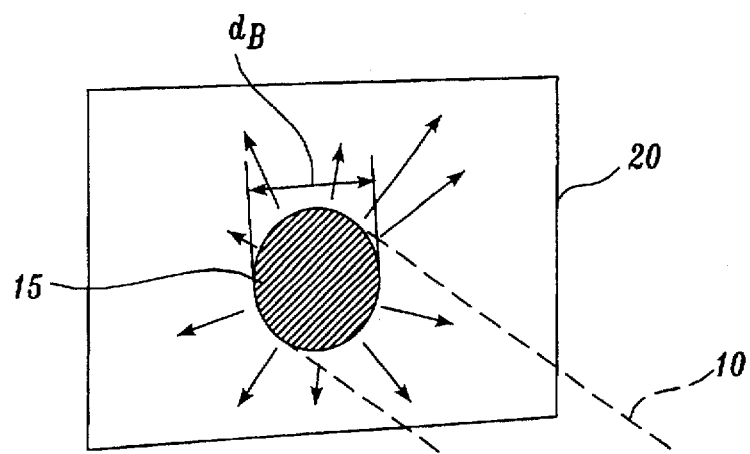
FIG. 1 is a schematic illustration of a prior art method of illuminating an extended rough surface.

In order to better understand the invention, the prior art will be briefly described. Referring to FIG. 1, a beam of light 10 illuminates a circular area 15 of an extended rough surface 20. Light travels, and scatters, in the direction of the arrows shown. The statistical properties of a speckle pattern arising from the scattering of light is determined by the diameter $d_B$ of the illuminating beam of light and the wavelength of the light $\lambda$.

Figure 2:
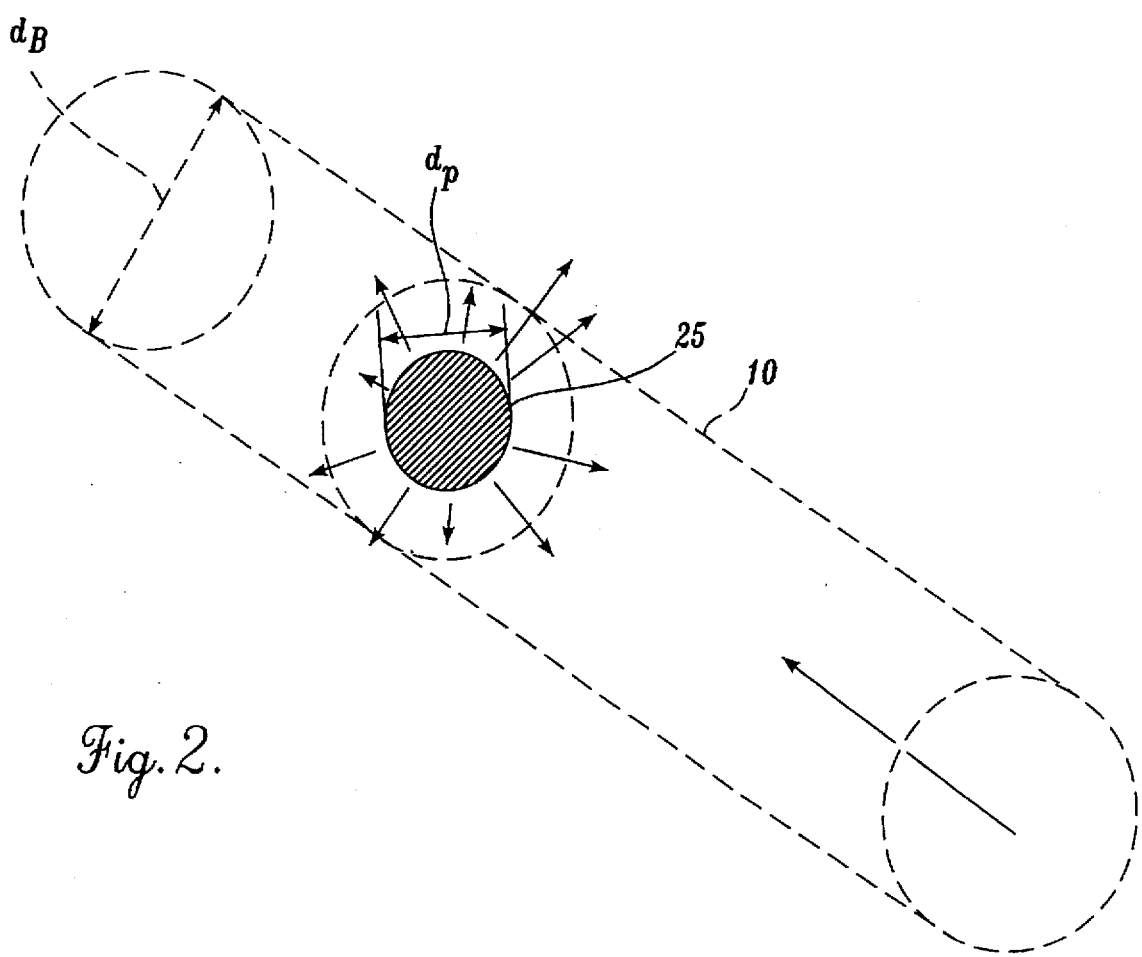
FIG. 2 schematically illustrates the illumination of an individual particle in accordance with the invention.

In contrast, the present invention is based on a different geometry, shown in FIG. 2. Thus, a beam of light 10 fully illuminates the entire surface of a particle 25 having a diameter $d_p$ and the same surface roughness as the surface 20 of FIG. 1. The useful electromagnetic radiation for the invention may be coherent, monochromatic, linear polarized, or a continuous or pulsed laser beam and be the like. The beam of light 10 is coherent and has a wavelength $\lambda$ that is much less than the diameter $d_p$ of the particle 25. Moreover, the beam diameter $d_B$ is much larger than the particle diameter $d_p$. As a result, the speckle pattern is now determined by the diameter $d_p$ of the scattering disk formed by the illumination of the surface of particle 25, instead of the beam diameter $d_B$, for any given wavelength $\lambda$. Thus, if the speckle pattern of a rough particle of unknown diameter $d_p^*$ is observed, and analyzed, then the diameter $d_p^*$ can be calculated from the statistical properties of the speckle pattern, in accordance with the invention.

Figure 3:
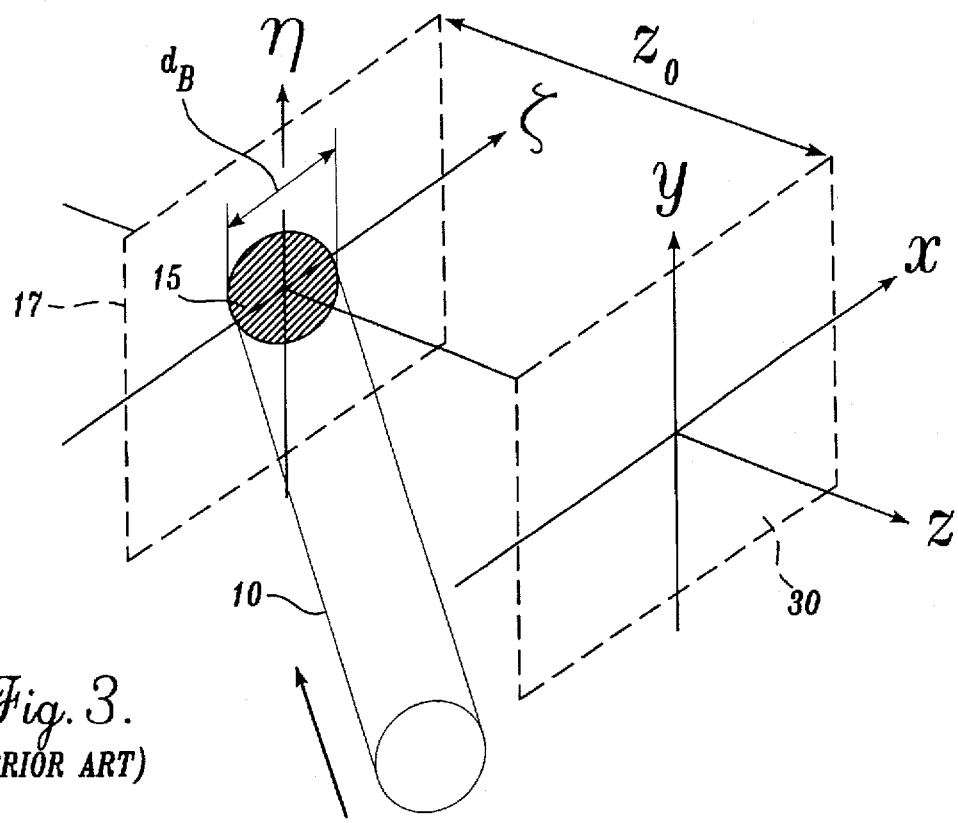
FIG. 3 is a schematic defining the coordinate system relating to the prior art shown in FIG. 1.

To further enhance an appreciation of the invention, attention is drawn to FIG. 3, illustrating the prior art. The geometry shown in FIG. 3 is that of a rough surface 15 that forms an object plane in this case the $\varepsilon\eta$ plane. A circular area of diameter $d_B$ of the object plane is illuminated by a coherent beam of light 10, of wavelength $\lambda$. The wavelength of the illuminating beam of light is chosen to be smaller than the peak-to-valley height of the rough surface, and larger than the correlation distance of the rough surface structure. Here the correlation length is the mean separation, measured parallel to the surface, between neighboring structure elements of the rough surface. The light scattered from the rough surface is observed at a distance $z_0$ in an observation plane 30. The observation plane 30 is placed at least a distance greater than $d^2/4\lambda$ from the particle producing the scatter. Due to interference arising from reflection of different microscopic surface elements, a speckle pattern can be observed in the image plane 30.

A perfectly polarized speckle pattern can be achieved by inserting a polarizer between the object (i.e., the particle)

and the observation plane 30. The probability density function of the intensity at any point $(x_0, y_0)$ in the observation plane 30 obeys negative exponential statistics. It is known that the standard deviation $\sigma_1$ of the intensity of the pattern is equal to the mean intensity $<I>$ of the speckle pattern. Therefore the contrast C which is equal to $\sigma_1/<I>$, of a fully developed polarized speckle pattern, is always equal to one. The dependence of speckle contrast on surface roughness is also known. Depending on the statistics of the surface height distribution of the scattering area, a monotonous decrease of contrast is predicted when the mean peak-to-valley-height of the surface profile is less than $\lambda/2$ and approaches zero.

In order to describe the spatial structure of a speckle pattern, second order statistical properties were investigated by Goodman (cited above), especially the two dimensional autocorrelation function $R_1(X_1, y_1, x_2, y_2)$ of the intensity distribution $I(x,y)$ of a polarized speckle in the observation plane. For a circular scattering spot in the object plane with diameter $d_B$ the autocorrelation function $R_1(r)$ given by Goodman as $$R_1(r) = <I>^2 \cdot [1 + |2 \cdot J_1(kd_B r)/(kd_B r)|^2] \quad (1)$$

In equation (1) the correlation parameter r is given by $r=[(\Delta x)^2+(\Delta y)^2]^{1/2}$, the parameter k is $k=\pi/\lambda z_0$ and $J_1$ denotes the first order Bessel-function. The "average width" of a speckle in the observation plane is taken to be the value of r where $J_1(kd_B r)$ first falls to zero. Denoting this distance $\delta r$, the average width of a speckle in a distance $z_0$ from the object plane caused by a circular scattering area with diameter $d_B$ under coherent illumination with wavelength $\lambda$ is $$\delta r = \frac{3.832}{\pi} \cdot \frac{\lambda z_0}{d_B} \quad (2)$$

Figure 4:
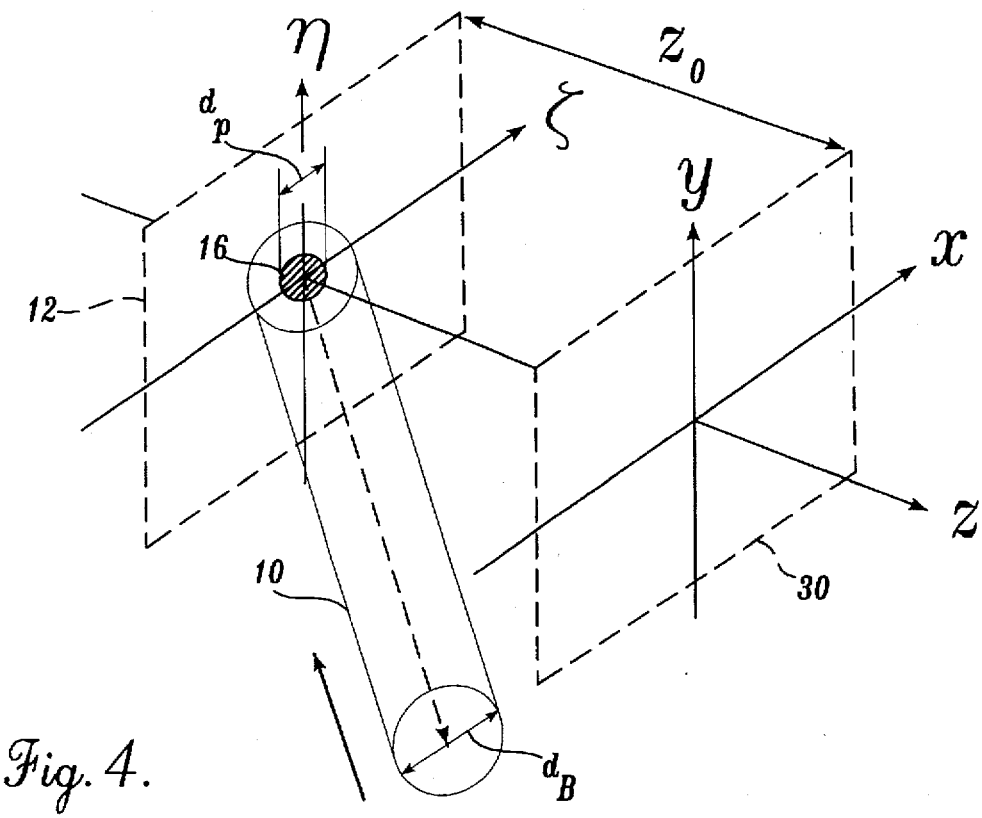
FIG. 4 is a schematic defining the coordinate system for the illumination method of FIG. 2 in accordance with the invention.

Based on these well known statistical properties of speckle patterns the new particle geometry measuring method will now be discussed, together with a preferred embodiment of the method. In contrast to the geometry of FIG. 3, the object plane 12 of FIG. 4, illustrating the invention, is only a mathematical plane and not filled with a rough surface. Instead, a single rough particle 16 of spherical shape is positioned in the object plane. The diameter $d_p$ of the particle is smaller than the diameter $d_B$ of the illuminating beam of light 10. Thus, the particle is fully illuminated by the beam of light. As a result, the second order statistical properties of the speckle pattern observed in the image plane 30 does not depend on the beam diameter $d_B$, but on the particle diameter $d_p$. If the angle $\alpha$ between the direction of the illuminating beam of light, and the Z-axis is sufficiently small, the spherical rough particle can be substituted, for the sake of explanation, by a circular area in the object plane. This area is the geometric shadow of the particle 16, with the same surface roughness as the particle. The statistical properties of the speckle pattern observed in the image plane remains unchanged by this substitution. Therefore, the described mathematical relations, governing the speckle pattern of an illuminated spot on a rough surface, can be used to determine the diameter of the illuminated rough particle.

For evaluation, at least a part of the intensity distribution $I(x, y)$ of one polarization component in the observation plane is detected, the autocorrelation function $R(r)$ is calculated using standard methods as described in detail by Goodman on page 38 of the article cited above. Finally, the width $\delta r$ is determined. When the illuminating light is coherent, and of wavelength $\lambda$, and the surface roughness of the particle is large as compared to $\lambda$, then the particle diameter $d_p$ may be found from equation (2), above:

$$d_p = \frac{3.832}{\pi} \cdot \frac{\lambda z_0}{\delta r} \quad (3)$$

This equation illustrates the underlying principle of measuring the particle geometric by the method of the invention. According to equation (3), a coarse speckle pattern is indicative of a small particle, and a finer pattern corresponds to a larger particle. Clearly, extension of this principle from one transverse dimension, as explained above, to the second transverse dimension is possible, and is within the scope of the present invention.

The surface roughness of the particle can be estimated from the calculation of the contrast $C=\sigma_1/<I>$ of the detected speckle pattern. A contrast value $C=1$ is found for particles with a mean peak-to-valley-height $h_{pv}>\lambda/2$. For $h_{pv}<\lambda/2$ the contrast C decreases, depending on the actual surface structure. Smooth particles, like liquid droplets or polished metal spheres, give a nearly homogenous distribution of intensity in the observation plane, their contrast is close to zero. By analysis of the measured contrast it can be verified that the particle under investigation fulfills the roughness requirement for particle size measurement by speckle observation. The monitoring of filtered liquids like clear water, for example, poses the problem of distinguishing light scattered by rough particles from light scattered by smooth particles or bubbles. Single rough particles in the fluid, e.g., caused by a broken filter, have to be detected, where air bubbles, that are usually found in the fluid, should not effect the detection. This problem can be solved by contrast analysis.

In most industrial applications where the size of rough particles relates to quality parameters of the process, the particle shape is not spherical, but can often be described as 37 more or less ellipsoidal." An example are particles found in the flue gas of a coal combustion process. Due to numerous collisions with flue walls or other particles their shape is usually comparable to ellipsoids with aspect ratios smaller than 3:1. To evaluate the geometric properties of ellipsoidal rough particles the basic method described above is extended.

Figure 5:
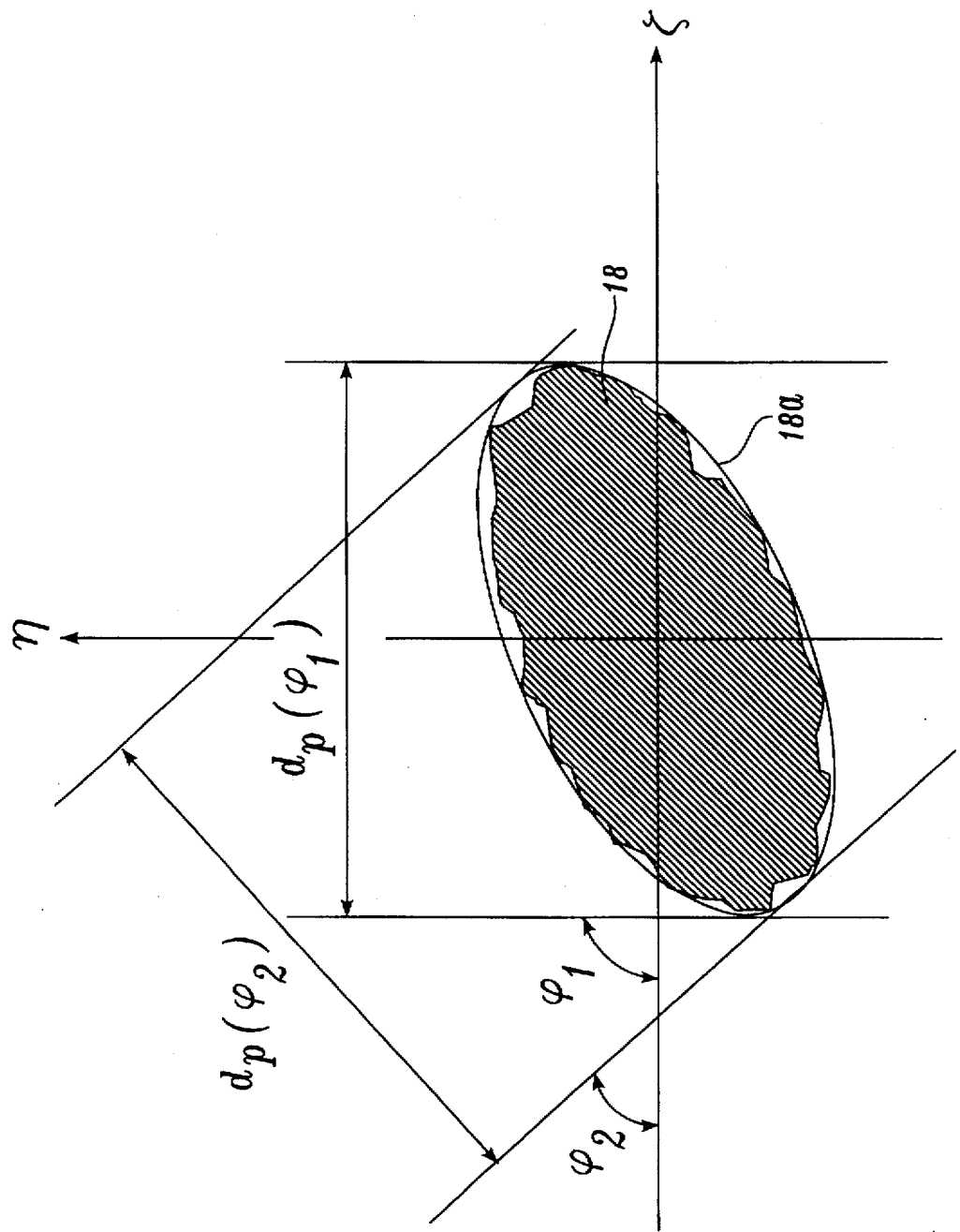
FIG. 5 is a schematic diagram showing the geometric shadow of a near ellipsoidal particle with rough surface.

The rough generally spherical particle is now replaced by a rough generally ellipsoidal particle. The diameter $d_B$ of the illuminating beam is chosen to be larger than the maximum length in any orientation of the ellipsoidal particle, therefore the particle is fully illuminated. Again, the particle may be replaced for calculation purposes by an elliptic area with identical surface structure in the object plane, this area being the geometric shadow of the ellipsoidal particle. The autocorrelation function of the intensity distribution in the observation plane does not show rotational symmetry. Instead the average speckle width $\delta r$ will now depend on an azimuthal angle $\phi$ under which the width $d_p$ is measured (see FIG. 5). The geometric shadow 18 of a rough ellipsoidal particle is approximated by an ellipse 18a. The one-dimensional autocorrelation function $$R_1(r,\phi) = <I>^2 \cdot [1 + |2 \cdot J_1(kd_p(\phi)r)/(kd_p(\phi)r)|^2] \quad (4)$$

has to be determined from the intensity distribution along a line in the observation plane inclined by an angle $\phi$ with respect to the x-axis of FIG. 4. The particle dimension $d_p(\phi)$ evaluated from RI is the tangential width of the elliptic area 18a as defined in FIG. 5. By evaluation of all tangential widths $d_p(\phi)$ for $\phi=0 \ldots \pi$ the length of the two semi-axis of the elliptical area and their orientation in the object plane are found as the minimum and maximum values of $d_p(\phi)$.

Figure 6:
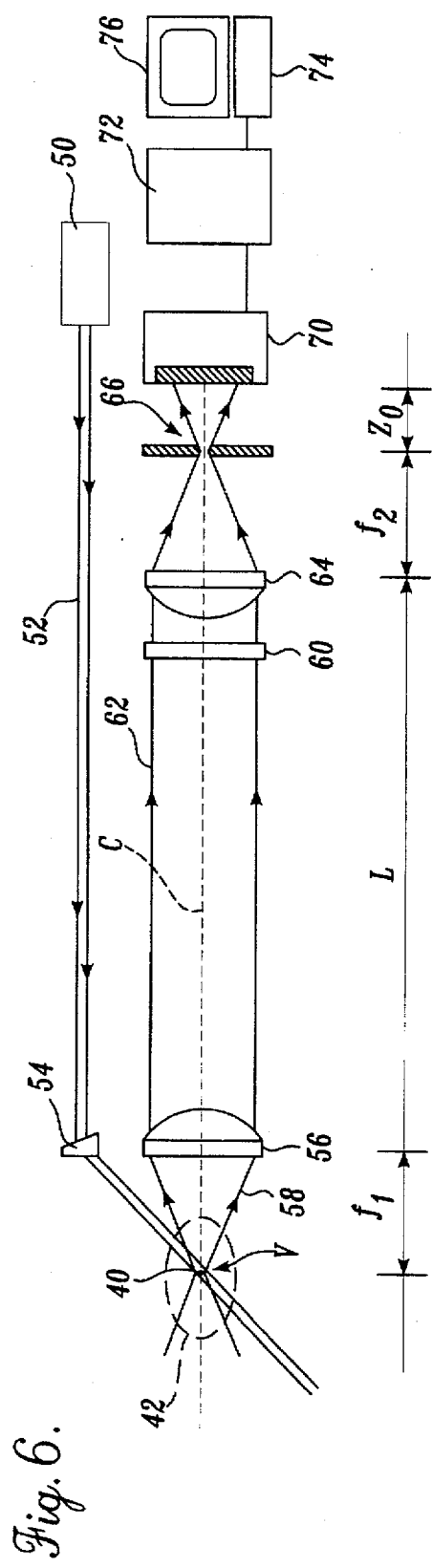
FIG. 6 is a schematic illustration of a system in accordance with the invention, for measuring geometric properties of an individual particle.
Figure 6A:
FIG. 6A is an enlarged schematic view of the zone surrounding the particle of FIG. 6.

A preferred embodiment of a system according to the present invention is shown in FIG. 6. A particle 40 is immersed in a liquid or gaseous fluid, in a zone 42 of a process being observed. A source of light 50 projects a coherent polarized beam of light 52 through a deflecting prism 54 to illuminate the particle 40. The width of the beam of light, as shown more clearly in FIG. 6A, is much larger then the largest dimension of the particle 40. Depending upon the type of process being observed, a continuous laser or a pulsed laser may be used. When particles are immersed in a moving fluid, a pulsed laser with short pulses is preferred so that particles do not move further then a small fraction of the illuminating wavelength during one illumination pulses.

The particle 40 is located in a volume formed by an intersection of the light beam 52 with the axis of a planoconvex lens 56. Thus, backscattered light falling onto the lens is collimated into a coherent beam 58 that passes through a polarizer 60, located behind the lens. Polarized light 62 then passes through a second plano-convex lens 64 that focuses the polarized light through a pinhole 66. Preferably, the second lens, spaced a distance L from the first lens, 56, has the same focal length as lens 56. The pinhole 66 is positioned within the focal distance $f_2$ of lens 64 and is centered on the optical axis C of the lens and polarizer optical system. Light passing through the pinhole impinges onto the surface of a detector 70 for the speckle pattern. The distance from the pinhole 66 to the detector 70 is $z_0$. Preferably, the detector 70 is a CCD-line or matrix camera. The camera is preferably connected to a frame grabber and an imaging processing unit 72 able to convert the one or two dimensional speckled pattern, measured by the detector, into binary data. This data is then supplied to a digital signal processor 74 that performs the correlations described above to calculate the particle size and surface roughness. The calculated particle size, and an image of the speckle pattern are displayed on a video display screen 76 (in electrical communication with the digital signal processor 74) and is stored on a storage device, such as a hard disk.

The optical part of the system shown in FIG. 6, using a pair of optical lenses, a polarizer and a pinhole, provides advantages over direct observation of the speckle pattern. For example, the detector 70 is located an additional distance L+2f (if $f_1=f_2=f$) away from the particle being observed. This is advantageous when the particles are in a hostile environment. The optics may be enclosed in a housing and shielded from the environment by an optical window. The detector and laser can then be located at a location more remote from the hostile environment. The use of the pinhole 66 assists in eliminating "noise." Without the pinhole, light from other particles located in the vicinity of the illuminating beam ("noise") could travel through to the detector and interfere with the speckle pattern of the particle being observed. Thus, the pinhole increases precision of size measurement. Clearly, the diameter of the pinhole, the focal length $f$ of the lenses, and the width of the laser beam is selected depending upon the concentration of particles to ensure a high likelihood that there is not more than one particle in the intersection volume V being observed. When two or more particles are in the intersection volume, they will form a joint speckle pattern that may lead to misleading size measurement.

In order to determine particle shape, the detector 70 is preferably a CCD-matrix camera with two dimensional resolution capability. When particle size distribution is the important parameter to be measured, and the shape of individual particles is a secondary concern, then a linear detector array is sufficient. When a large number of particles with arbitrary orientations are measured, a mean particle size being the average over tangential widths $d_p(\phi)$ and a mean particle size distribution are calculated from the distribution of tangential widths $d_p(\phi°)$ for a fixed angle $\phi°$.

Figure 7:
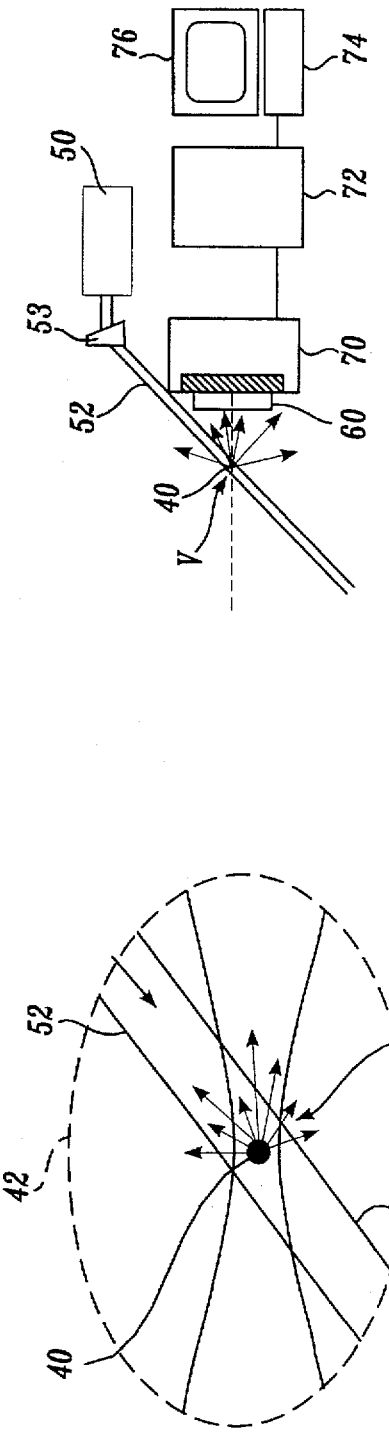
FIG. 7 is a schematic view of an alternative embodiment, in accordance with the invention, of a system for measuring geometric properties of an individual particle.

In an alternative embodiment, shown in FIG. 7, the pair of lenses and the pinhole are eliminated. Thus, a source of illumination 50 provides a beam 52 that is directed through a prism 54 into a zone V containing one particle 40. Backscattered light passes the polarizer 60 attached to the front of the camera and impinges onto a detector 70 that transmits an electronic signal to an image processing unit 72. The processing unit in turn converts the speckle distribution to a dataset that is transmitted to a digital signal processor 74 for correlation analysis. As before, the results of the analysis can be displayed on a visual display screen 76. However, as explained above, the embodiment of FIG. 6 is preferred.

The following example is illustrative of certain aspects of the invention, and does not limit or define the invention as described above and claimed herebelow.

EXAMPLE

An assembly in accordance with FIG. 6 was constructed and numerous test measurements were carried out on individual rough particles. Referring to FIG. 6, the source of light 50 was a linear polarized helium neon laser ($\lambda$=632.8 nanometers). Each of the plano-convex lenses, 56 and 64 had a diameter of 50 millimeters, a focal length of 100 millimeters. The lenses were spaced a distance of 500 millimeters apart. The diameter of the pinhole 66 was 0.5 millimeters. The detector 70 was a CCD-matrix camera with a 256×256 image element (pixel) capability. The pixel size was 11×11 square microns. The camera was placed a distance of 20 millimeters from the pinhole.

Using this equipment, the speckle pattern of single rough particles in a size range from about 10 microns to about 200 microns was detected and analyzed using a personal digital computer. Tangential widths of the particles were calculated from the speckle pattern, and compared to microscopic measurements of these particles. The results of the method and system of the invention did not differ by more than 5% from the standard microscopy measurements.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of measuring geometric properties of individual particles one at a time in a volume containing many particles, the method comprising:

(a) illuminating the volume containing many particles including an individual particle to be measured with a beam of electromagnetic radiation, the beam having a width wider than a largest dimension of the individual particle to be measured;

(b) detecting an intensity distribution of electromagnetic radiation back-scattered from the individual particle in the volume; and (c) analyzing the detected intensity distribution to determine the geometric properties of the individual particle.

2. The method of claim 1, further comprising providing an image of the geometric properties produced by the step of analyzing.

3. The method of claim 1, further comprising polarizing the electromagnetic radiation back-scattered from the individual particle before detecting the intensity distribution of the back-scattered radiation.

4. The method of claim 1, further comprising, before the step (b) of detecting, collimating back-scattered electromagnetic radiation from the individual particle through at least one optical lens.

5. The method of claim 1, wherein the analyzing comprises applying first and second order statistical techniques to the detected intensity distribution of electromagnetic radiation.

6. The method of claim 1, wherein a wavelength of the illuminating beam of electromagnetic radiation is small compared to surface roughness of the individual particle.

7. The method of claim 6, wherein the analyzing comprises determining an effective diameter of the individual particle using the equation:

$$d_p = \frac{3.832}{\pi} \cdot \frac{\lambda z_0}{\delta r}$$

where:
$d_p$=effective particle diameter
$\lambda$=wavelength of the electromagnetic radiation
$z_0$=distance of the object plane from the particle
$\delta r$=correlation distance where the value of the autocorrelation function, RI(r), of the detected intensity distribution first decreases to zero.

8. The method of claim 7, wherein the individual particle is substantially ellipsoidal in shape, and the analyzing comprises determining dimensions of said particle along the azimuthal direction $\phi$ of the intensity distribution.

9. The method of claim 1, further comprising before the step (b) of determining, focusing the back-scattered electromagnetic radiation from the individual particle through a lens and a pinhole aligned along an optical axis of the lens.

10. The method of claim 1, wherein the step of analyzing comprises analyzing with a digital signal processor.

11. The method of claim 1, wherein the illuminating is by a beam of electromagnetic radiation projected from a source of radiation through a prism into the volume containing the individual particle to be measured.

12. The method of claim 1, wherein the illuminating is with electromagnetic radiation selected from the group consisting of the infrared, ultraviolet, and visible wavelengths of light.

13. A system for measuring the geometry of individual small particles within a volume containing many particles, the system comprising:
   (a) a source of electromagnetic radiation;
   (b) means for directing radiation from the source into the volume containing many particles, including an individual particle to be measured;
   (c) means for detecting a back-scattered intensity distribution of electromagnetic radiation from the individual particle; and
   (d) a digital signal processor for analyzing the detected intensity distribution of the individual particle to determine geometric properties of said particle.

14. The system of claim 13, further comprising imaging means, in electrical communication with the digital signal processor, for providing an image of the individual particle.

15. The system of claim 13, further comprising at least one optical lens, the lens collimating back-scattered electromagnetic radiation from the individual particle before the back-scattered radiation reaches the means for detecting.

16. The system of claim 15, further comprising a pinhole, the pinhole interposed between the at least one lens and the means for detecting a back-scattered intensity distribution of electromagnetic radiation.

17. The system of claim 13, further comprising a polarizer for back-scattered electromagnetic radiation, the polarizer interposed between the at least one lens and the means for detecting a back-scattered intensity distribution of electromagnetic radiation.

18. The system of claim 13, wherein the source of radiation supplies coherent monochromatic radiation.

19. The system of claim 13, wherein the source of radiation is a source of a laser beam.

20. The system of claim 13, wherein the source of radiation is a source of a pulsed laser beam.

21. The system of claim 13, wherein the source is a source of linear polarized radiation.

22. A method of measuring geometric properties of individual particles, in situ and in real times, the method comprising:
   (a) illuminating a sample volume of a fluid containing an individual particle to be measured with electromagnetic radiation, the radiation having a wavelength less than peak-to-valley dimensions of roughness of the individual particle and a beam width wider than a largest dimension of the individual particle;
   (b) filtering backscattered radiation from the individual particle through a pin hole;
   (c) detecting an intensity distribution of backscattered radiation exiting the pin hole; and
   (d) analyzing the detected radiation to determine geometric properties of the individual particle, with a digital signal processor.

23. The method of claim 22, further comprising storing data about the geometric properties of the individual particle on a storage device.

24. The method of claim 22, further comprising displaying the determined geometric properties of the individual particle on a visual display screen.

* * * * *

UNITED STATES PATENT AND TRADEMARK OFFICE
CERTIFICATE OF CORRECTION

PATENT NO.    : 5,748,311
DATED         : May 5, 1998
INVENTOR(S)   : O. Hamann et al.

It is certified that error appears in the above-identified patent and that said Letters Patent is hereby corrected as shown below:

| COLUMN | LINE |  |
|---|---|---|
| 9 (Claim 8, | 28 line 4) | Before "intensity" insert --detected-- |
| 10 (Claim 22, | 30 line 2) | "times," should read --time,-- |

Signed and Sealed this

Fifteenth Day of September, 1998

Attest:

BRUCE LEHMAN

*Attesting Officer*          *Commissioner of Patents and Trademarks*